United States Patent [19]

Ito et al.

[11] Patent Number: 5,354,473

[45] Date of Patent: Oct. 11, 1994

[54] METHOD FOR CONCENTRATING A SOLUTE BY COUNTERCURRENT CHROMATOGRAPHY

[75] Inventors: Yoichiro Ito; Hans J. Cahnmann, both of Bethesda, Md.

[73] Assignee: The United States of America as represented by the Departent of Health and Human Services, Washington, D.C.

[21] Appl. No.: 123,033

[22] Filed: Sep. 20, 1993

Related U.S. Application Data

[63] Continuation of Ser. No. 946,613, Sep. 18, 1992, abandoned.

[51] Int. Cl.$^5$ .............................................. B01D 15/08
[52] U.S. Cl. ................................... 210/635; 210/657; 210/198.2
[58] Field of Search ............... 210/635, 656, 657, 659, 210/198.2, 96.1, 101

[56] References Cited

U.S. PATENT DOCUMENTS

| | | | |
|---|---|---|---|
| 3,775,309 | 11/1973 | Ito | 210/657 |
| 3,856,669 | 12/1974 | Ito | 210/657 |
| 3,994,805 | 11/1976 | Ito | 210/657 |
| 4,051,025 | 9/1977 | Ito | 210/657 |
| 4,058,460 | 11/1977 | Ito | 210/657 |
| 4,321,138 | 3/1982 | Ito | 210/657 |
| 4,324,661 | 4/1982 | Ito | 210/657 |
| 4,430,216 | 2/1984 | Ito | 210/198.2 |
| 4,478,713 | 10/1984 | Girot | 210/198.2 |
| 4,487,693 | 12/1984 | Ito | 210/657 |
| 4,615,805 | 10/1986 | Ito | 210/657 |
| 4,714,554 | 12/1987 | Ito | 210/657 |
| 4,753,734 | 6/1988 | Ito | 210/657 |
| 4,840,730 | 6/1989 | Saxena | 210/659 |
| 4,857,187 | 8/1989 | Ito | 210/657 |
| 4,859,342 | 8/1989 | Shirasawa | 210/659 |
| 5,024,758 | 6/1991 | Ito | 210/657 |

OTHER PUBLICATIONS

Cahnmann, "Synthesis and Characterization of N-Bromoacetyl-3-3',5-triiodo-L-thyronine", Journal of Chromatography, vol. 538, No. 1, Jan. 18, 1991, pp. 165–175.

Y. Ito et al., "The Elution Centrifuge Applied to Countercurrent Chromatography", Analytical Biochemistry, vol. 49, No. 1, Sep. 1972 pp. 1–8.

W. Conway, "Chromatographic Theory", Dept. of Pharm. and Medical Chemistry, State University of New York, 1990, pp. 195–219.

Y. Ito et al., "Countercurrent Chromatography—Theory and Practice", Principles and Instrumentation of CCC, Marcel Dekker, Inc., New York, pp. 330–421 (1988).

*Primary Examiner*—Ernest G. Therkorn
*Attorney, Agent, or Firm*—Birch, Stewart, Kolasch & Birch

[57] ABSTRACT

A method for concentrating a solute from a mixture by countercurrent chromatography, by introducing a stationary phase into a countercurrent chromatographic centrifuge, introducing a sample of a mixture containing a solute into the centrifuge, introducing a sufficient quantity of an elution peak sharpening agent into the centrifuge, introducing a mobile phase into the centrifuge, and performing countercurrent chromatographic centrifugation. The eluting fractions containing the concentrated solute are identified and collected.

19 Claims, 12 Drawing Sheets

1

METHOD FOR CONCENTRATING A SOLUTE BY COUNTERCURRENT CHROMATOGRAPHY

This application is a continuation of application Ser. No. 07/946,613 filed on Sep. 18, 1992, now abandoned.

BACKGROUND OF THE INVENTION

Countercurrent chromatography (CCC) is a liquid-liquid partition chromatography method. The partitioning process takes place in an open column space which is free of any solid support matrix, and the method avoids the considerable adsorptive sample loss and tailing of solute peaks which may occur when a solid support matrix is present. Consequently, the method usually yields symmetrical solute peaks in isocratic elution, where peak width naturally increases with the retention time.

Countercurrent chromatographic theory, as well as apparatus for carrying out the method, is described in Y. Ito, *Principle and Instrumentation of Countercurrent Chromatography*, in Countercurrent Chromatography: Theory and Practice 79–442 (N. B. Mandava and Y. Ito eds. 1988); and in W. D. Conway, Countercurrent Chromatography: Apparatus, Theory and Applications (1990). See also, Ito et al., 49 Anal. Biochem. 1–8 (1972), and U.S. Pat. No. 4,753,734.

A disadvantage associated with CCC is the increased peak width associated with increased retention time of the solute. This increased peak width makes detection of the solute more difficult, and requires a larger volume of eluate to be collected and processed in order to obtain a maximum yield of solute. Nevertheless, increased retention time is desirable in order to avoid coeluting impurities with the solute.

While sharp elution peaks have been noted with CCC, there has been no description or suggestion in the art of a method for obtaining a sharp elution peak while maintaining increased retention time, in the countercurrent chromatography of a solute. See H. J. Cahnmann et al., 538 J. Chromatog. 165–167 (1991).

SUMMARY OF THE INVENTION

Accordingly, it is an object of the present invention to provide a method for obtaining a sharp elution peak of a solute being concentrated by countercurrent chromatography, without decreasing the retention time of said solute.

It is also an object of the present invention to provide a process for concentrating a solute by countercurrent chromatography, which requires that a relatively small volume of eluate be collected and processed to maximize the yield of the desired solute.

It is also an object of the present invention to obtain said concentrated solute while allowing sufficient retention time of said solute to avoid coeluting impurities with said solute.

These and other objects are accomplished by providing a method for concentrating a solute from a mixture by countercurrent chromatography, comprising:

(a) introducing a stationary phase into a countercurrent chromatographic centrifuge;
(b) introducing a sample of a mixture containing a solute into the countercurrent chromatographic centrifuge;
(c) introducing a sufficient quantity of an elution peak sharpening agent into the countercurrent chromatographic centrifuge;
(d) introducing a mobile phase into the countercurrent chromatographic centrifuge;
(e) performing countercurrent chromatographic centrifugation of the mobile phase and eluting fractions of the mobile phase from the countercurrent chromatographic centrifuge; and
(f) identifying and collecting the eluting fractions containing the concentrated solute.

The present invention also provides a method for concentrating a solute from a mixture by countercurrent chromatography, wherein the elution peak sharpening agent is an acid or a base, and wherein this elution peak sharpening agent may be introduced with the sample mixture, or introduced into the stationary phase. Preferably, the solute is an organic acid or an organic base. If an organic acid is to be used as the solute, then the elution peak sharpening agent is preferably also an organic acid, and if an organic base is to be used as the solute, then the elution peak sharpening agent is preferably also an organic base.

When the elution peak sharpening agent is introduced with the sample, those eluting fractions containing the concentrated solute are preferably identified and collected by monitoring the pH of the eluting fractions, and collecting those fractions which elute from the time when the pH begins to increase rapidly, if an acidic elution peak sharpening agent is used, until the time that the pH becomes relatively constant. Similarly, if a basic elution peak sharpening agent is used, the fractions that are collected are those eluting from when the pH begins to decrease rapidly to when the pH becomes relatively constant.

When the elution peak sharpening agent is introduced with the stationary phase, those eluting fractions containing the concentrated solute are identified and collected by monitoring the pH of the eluting fractions, and collecting those fractions eluting during the transitional zone between two different, approximately constant pH levels, or plateaus.

DETAILED DESCRIPTION OF THE INVENTION

Figure 1:
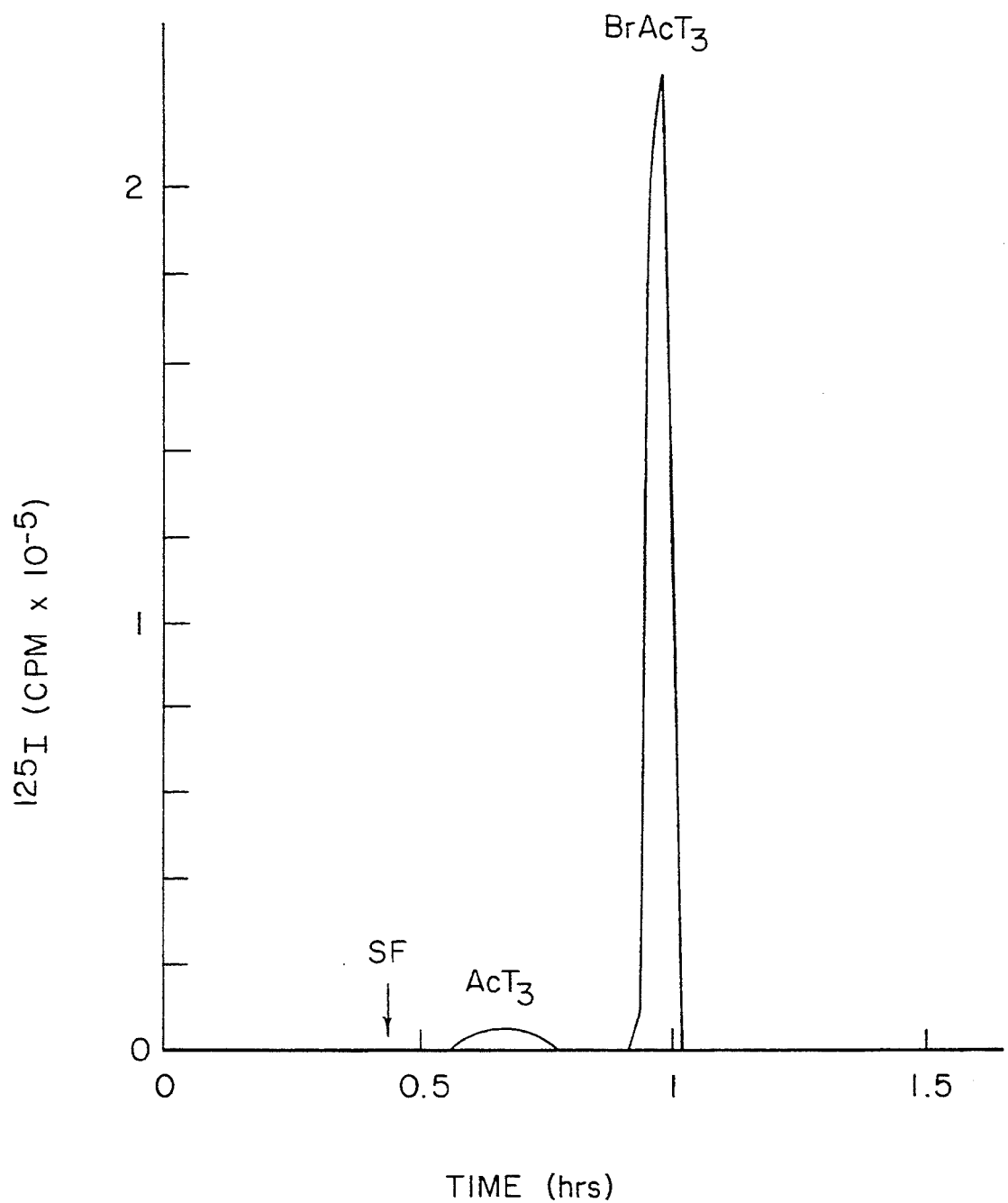
FIG. 1 is a chromatogram of BrAcT$_3$ obtained with a standard two-phase solvent system showing a sharp peak profile.

The countercurrent chromatographic centrifuge used in the present invention may be any centrifuge suitable for countercurrent chromatography. Examples of countercurrent chromatographic centrifuges are described in Y. Ito, *Principle and Instrumentation of Countercurrent Chromatography*, in Countercurrent Chromatography: Theory and Practice 79-442 (N. B. Mandava and Y. Ito eds. 1988); W. D. Conway, Countercurrent Chromatography: Apparatus, Theory and Applications (1990); Ito et al., 49 Anal. Biochem. 1-8 (1972); and U.S. Pat. No. 4,753,734.

More particularly, the countercurrent chromatographic centrifuge usually comprises a coiled column, supported by a column holder. The column is preferably a single piece of PTFE (polytetrafluoroethylene). The column and column holder are rotatably disposed on a rotary frame, such that both the column holder and the rotary frame rotate about their respective axes during centrifugation. It is preferred that the column holder undergo one rotation about its own axis per revolution around the central axis of the rotary frame. It is also preferred that both rotations be in the same direction. The rotational speed of the centrifuge is preferably 800-1000 rpm.

The centrifuge is prepared by introducing a stationary phase into the column. This stationary phase is generally a non-polar organic solvent or mixture of at least one non-polar organic solvent, which has been equilibrated with the mobile phase, which is generally a polar solvent, and then separated.

Suitable organic solvents for use in forming the stationary phase include hexane, ethyl acetate, methanol, methyl tertiary butyl ether (MTBE), and acetonitrile. Suitable aqueous solutions for forming the mobile phase include water, and an aqueous solution of ammonium acetate. More preferred stationary phases and mobile phases include a mixture of hexane, ethyl acetate, methanol, and an aqueous solution of 15 mM ammonium acetate at a volume ratio of 1:1:1:1 or 4:5:4:5, where the pH of the ammonium acetate solution was adjusted by adding acetic acid, and a mixture of MTBE, acetonitrile, and water at a volume ratio of 4:1:5. In each case, the mixture is thoroughly equilibrated at room temperature by repeated mixing and degassing, and the phases are allowed to separate shortly before use. The organic phase is loaded into the column as the stationary phase, the elution peak sharpening agent and the sample solution to be concentrated are introduced into the column, and the aqueous phase is introduced into the column during centrifugation as the mobile phase.

Sample solutions are prepared by dissolving the crude solute containing mixture into an aliquot of solvent, preferably 2 to 4 ml of the solvent used to prepare the stationary phase and the mobile phase. The solute to be concentrated is preferably an organic compound, and may be an acid or a base, but is preferably an organic acid. More particularly, said organic acid solutes may include N-bromacetyl-3,3',5-triiodo-L-thyronine (T$_3$), indole auxins, DNP-L-leucine, and mixtures thereof.

The elution peak sharpening agent may be any compound that causes a pH profile to form across the stationary phase-mobile phase boundary. In general, if the solute is acidic, an acidic elution peak sharpening agent is used, and if the solute is basic, a basic elution peak sharpening agent is used. Preferred acidic elution peak sharpening agents include carboxylic acids, more particularly aliphatic acids including bromoacetic acid, trifluoroacetic acid, acetic acid, propanoic acid, butanoic acid, and the like.

The elution peak sharpening agent may be introduced to the column either with the sample solution, or with the stationary phase. After introduction of the elution peak sharpening agent and the introduction of the sample solution, the mobile phase is introduced into the column, and centrifugation is initiated. The mobile phase is preferably continuously supplied to the column during the centrifugation process.

The present invention is further illustrated by the following Examples, which are not intended to limit the scope of the invention.

EXAMPLES

Reagents

Chemicals used: T$_3$ and L-thyroxine (T$_4$), 98–99% pure (Aldrich, Milwaukee, Wis.); [3'-$^{125}$I]T$_3$, carrier-free (2200 Ci/mmol) and [3',5'-$^{125}$I]T$_4$, carrier-free (4400 Ci/mmol) (DuPont/NEN110X and 111X, respectively); hexane, methanol and trifluoroacetic acid (TFA) (HPLC grade from Burdick and Jackson, Muskegon, Mich.); ethyl acetate (HPLC grade from Burdick and Jackson for CCC fractionation and reagent grade for bromoacetylation); 1,2-dimethoxyethane (ethylene glycol dimethylether) 99.9%, HPLC grade and bromoacetyl bromide (BrAcBr), 98+% from Aldrich; HBr (48%), bromoacetic acid and methyl bromoacetate (reagent grade) from Fisher Scientific, Pittsburgh, Pa.; ammonium acetate (reagent grade) from Mallinckrodt, Paris, Ky.; indole auxins including indole-3-acetamide (IA), indole-3-acetic acid (IAA), and indole-3-butyric acid (IBA) from Sigma Chemicals, St. Louis, Mo.

Bromoacetylation of T$_3$ and T$_4$

Addition of 2ml of BrAcBr (in a hood) to a suspension of 263 mg (0.4 mmol) of T$_3$ in 100ml of ethyl acetate caused dissolution of the T$_3$. The resulting yellowish solution, after addition of a small boiling chip (amphoteric alundum granules, Hengar Co., Philadelphia, Pa.) was heated rapidly to incipient boiling (2 min) and then refluxed for an additional 10 min. This resulted in a color change from yellowish to nearly colorless. The reaction was carried out in a 200-ml round-bottom flask equipped with a short reflux condenser (8 cm) which was connected via an empty safety bottle to a wash bottle containing 1M NaOH in 50% ethanol to absorb escaping BrAcBr and HBr. The reaction was terminated by cooling in ice water, followed by addition of 2 ml of methanol to destroy excess BrAcBr. The reaction mixture was concentrated under reduced pressure to about 2 ml using a rotary evaporator (Büchi Rotovapor R) and a water bath not exceeding 30° C. This concentrate contains, in view of later findings, products that affect the chromatograph of $BrAcT_3$ (see below). Higher temperatures during concentration or prolonged evaporation times result in partial decomposition and aggregate formation of $BrAcT_3$. Aliquots of the concentrate were fractionated by CCC as described below.

In a few experiments, a minute amount of $[3'\text{-}^{125}I]T_3$ was used in addition to the unlabelled $T_3$. The labeled $BrAcT_3$ thus formed served as a convenient marker for chromatographic detection and yield determination. Bromoacetylation of $T_4$ was carried out similarly except that ethyl acetate was replaced with 1,2-dimethoxyethane and the reaction was terminated after rapid heating to incipient boiling (2 min).

A blank bromoacetylation was also carried out in which only solvent and reagent were used, but no $T_3$ or $T_4$.

CCC Fractionation

All separations were performed with a commercial model of the high-speed CCC centrifuge (Ito Multilayer Separator/Extractor from P.C. Inc., Potomac, Md., USA). The apparatus holds a multilayer coil semi-preparative separation column and a counterweight symmetrically on the rotary frame at a distance of 10 cm from the central axis of the centrifuge. The multilayer coil consists of a 165 m long, single piece of PTFE (polytetrafluoroethylene) tubing with a total capacity of about 325 ml. The column holder undergoes a particular mode of planetary motion: one rotation about its own axis per one revolution around the central axis of the centrifuge, both in the same direction. Although the maximum revolution speed of the centrifuge is 1000 rpm, 800 rpm was applied throughout the present experiments.

The two-phase solvent system was prepared by mixing hexane, ethyl acetate, methanol and an aqueous solution of 15 mM ammonium acetate at a volume ratio of 1:1:1:1 or 4:5:4:5 where the pH of the ammonium acetate solution was adjusted by adding acetic acid. The solvent mixture was thoroughly equilibrated at room temperature in a separatory funnel by repeated shaking and degassing and the two phases were separated shortly before use.

Sample solutions were prepared by dissolving the sample, i.e. the above-mentioned aliquot of the concentrate of crude $BrAcT_3$ or $BrAcT_4$ in 2 to 4 ml of the above 1:1:1:1 solvent. In some occasions, CCC-purified fractions of these compounds and a mixture of indole auxins were also used as samples.

In each separation, the entire column was first filled with the stationary phase followed by sample injection through the sample port. The mobile aqueous phase was then pumped into the head of the column at a flow rate of 3 ml/min while the apparatus was spun at 800 rpm. The effluent from the outlet of the column was continuously monitored with a uv monitor (Uvicord S, LKB Instruments, Bromma, Sweden) at 280 nm and collected in glass tubes (12×75 mm) to obtain 3-ml fractions using an Ultrorac fraction collector (LKB Instruments). After the desired $BrAcT_3$ or $BrAcT_4$ peak had been eluted, the run was terminated and the column contents were collected into a graduated cylinder to determine the volume of the stationary phase retained in the column.

Analysis of CCC Fractions

In separation of radioactive samples, the radioactivity of each fraction was measured with a gamma scintillation counter (Auto-Gamma 500 Series, Packard Instruments, Downers, Ill.). The pH of each fraction was determined by a portable pH meter (Accumet Portable Laboratory, Fisher Scientific, Pittsburgh, Pa.) or a model 25 pH meter (Radiometer Copenhagen).

Determination of Partition Coefficient (K)

The partition coefficients for $T_3$ and $T_4$ derivatives and indole auxins were determined by using two different methods. They are expressed as $K = C_L/C_u$, i.e., solute concentration in the mobile phase divided by that in the stationary phase. In the first method, each sample was separately equilibrated between two phases in a test tube by stirring the contents with a vortex mixer. An aliquot of each phase was diluted with methanol to measure the uv absorbance at 280 nm. For some $T_3$ or $T_4$ derivatives, the K values were also determined by measuring the radioactivity of $^{125}I$ in each phase. In the second method, K values were computed from the chromatogram using the following equation:

$$K = (V_C - R_{SF})/(R - R_{SF}) \qquad (1)$$

where R is the retention volume of the peak maximum; $V_c$, the total column capacity; and $R_{SF}$, the retention volume of the solvent front which corresponds to the volume of the mobile phase in the separation column.

"SF" in all chromatograms indicates the solvent front.

Example 1

FIG. 1 shows the CCC elution profile of the reaction product obtained by bromoacetylation of $T_3$, monitored by the radioactivity of $^{125}I$. The separation was performed with a two-phase solvent system composed of hexane, ethyl acetate, methanol and 15 mM ammonium acetate (pH 4) at a volume ratio of 1:1:1:1 and by eluting the lower aqueous phase at a flow rate of 3 ml/min. The sample chromatographed was a crude bromoacetylation mixture (from 0.1mmol $T_3$ and a minute amount of $[^{125}I]T_3$) in 4 ml of solvent consisting of equal volumes of upper and lower phases; the mobile phase was the lower aqueous phase (pH 5.2); the centrifuge was revolved at 800 rpm; 70% of the total column capacity was retained as the stationary phase. In this chromatogram, the main $BrAcT_3$ shows a much sharper profile than the earlier eluting impurity peak which was shown by mass spectrometry (3) to be N-acetyl-$T_3$ ($AcT_3$).

Example 2

Figure 2:
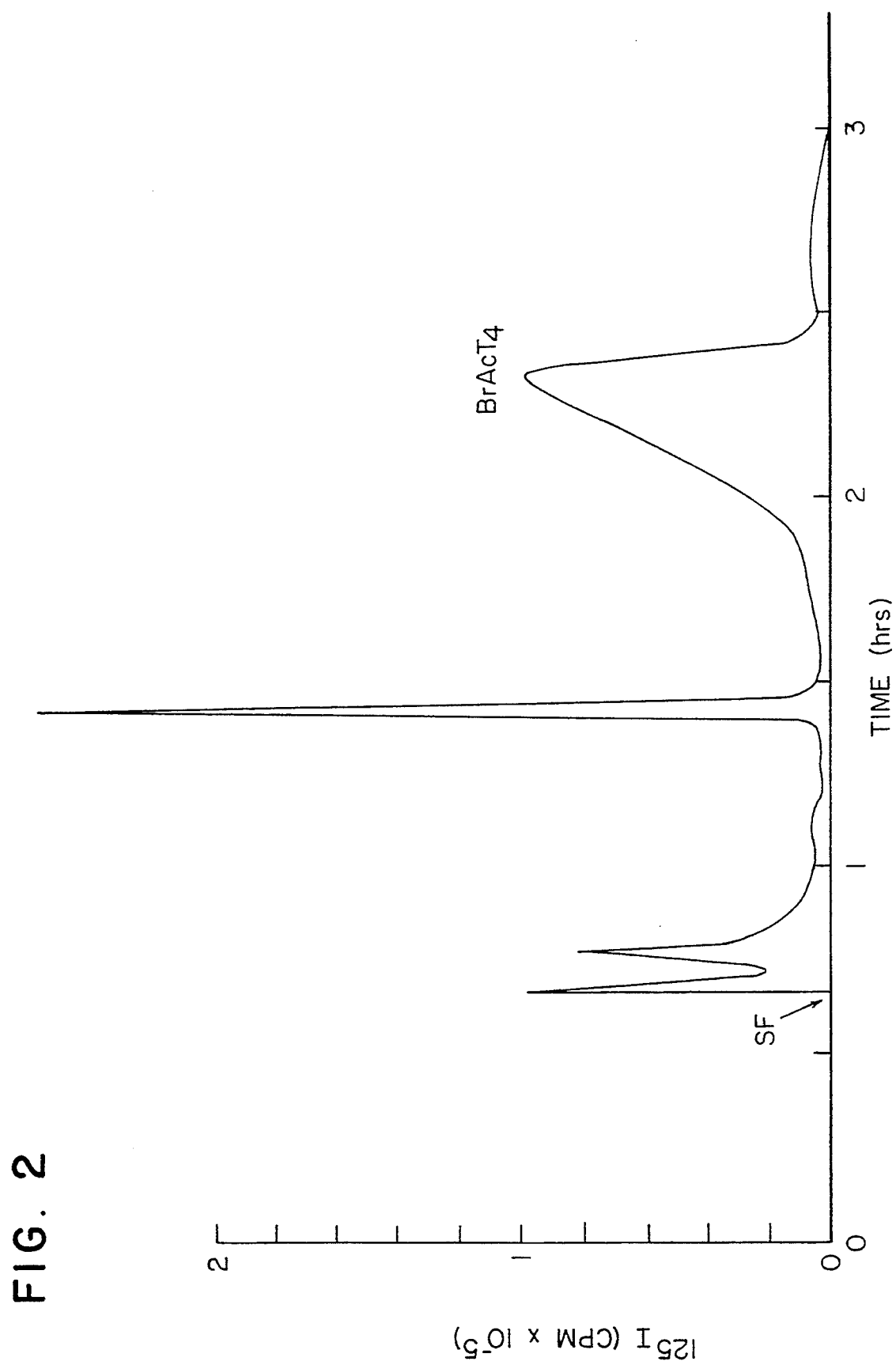
FIG. 2 is a chromatogram of BrAcT$_4$ obtained with a modified solvent system.

FIG. 2 similarly illustrates the CCC elution profile of the reaction product obtained by bromoacetylation of $T_4$ and by using a modified solvent ratio of 4:5:4:5 (pH 4). The sample chromatographed was the concentrate obtained after bromoacetylation of 0.1 mmol $T_4$, diluted to 4 ml with solvent consisting of equal volumes of each phase. Retention of the stationary phase was 60%. In contrast to the chromatogram in FIG. 1, the major peak ($BrAcT_4$) has a normal broad, and somewhat skewed shape while a preceding peak is unusually sharp like the $BrAcT_3$ peak in FIG. 1. HPLC analysis, mass spectrometry, and rechromatography with CCC revealed that this peak, in spite of its sharp appearance, actually represents a mixture of several components.

Example 3

Figure 3:
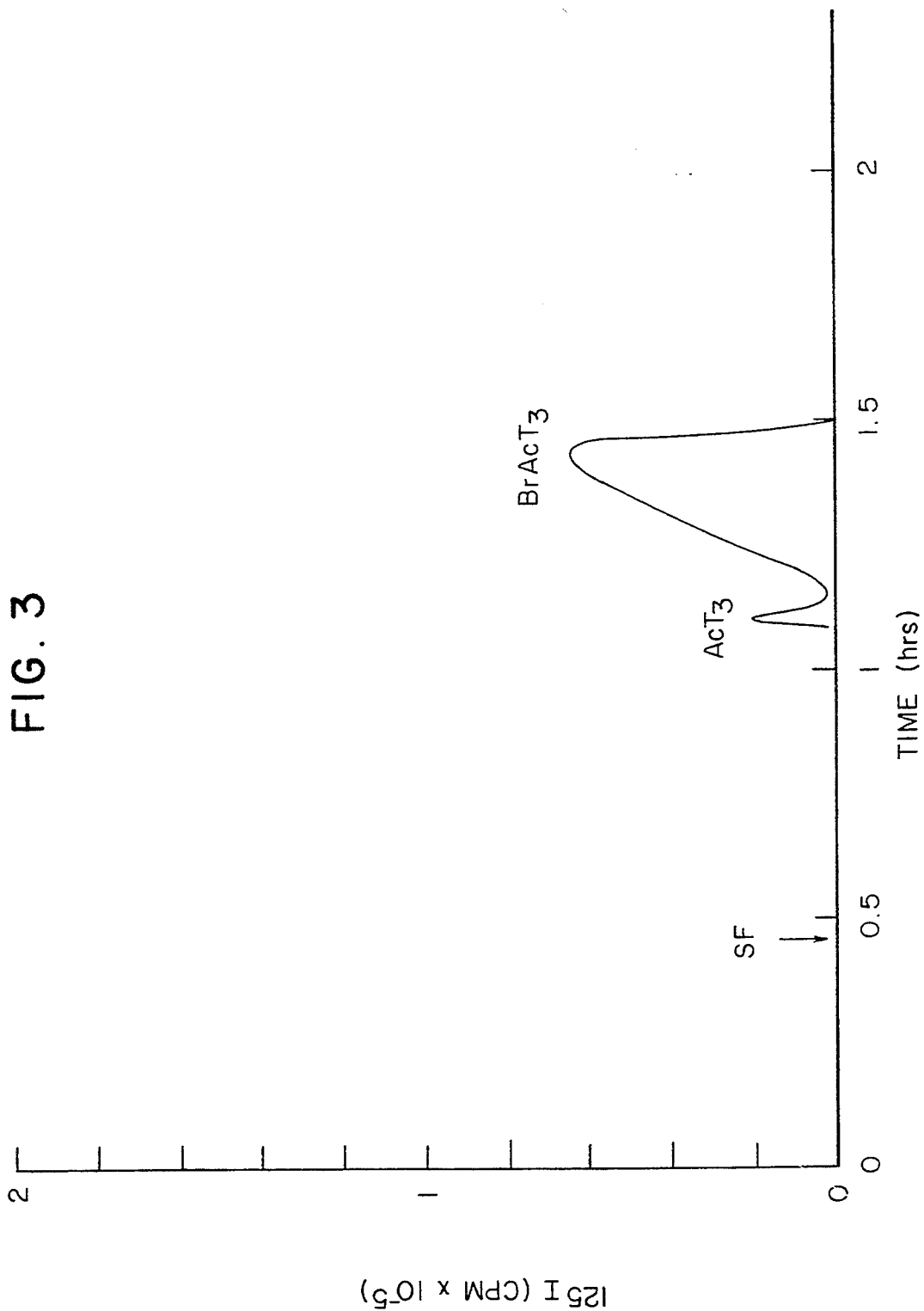
FIG. 3 is a chromatogram of BrAcT$_3$ obtained with a modified solvent system.

FIG. 3 is a chromatogram of $BrAcT_3$ obtained with a modified solvent system. Note that $BrAcT_3$ eluted in a broad peak whereas $AcT_3$, which formed broad peak in the standard solvent system (Example 1), shows a sharpened peak profile. Experimental conditions were identical to those described in Example 1, except that the solvent volume ratio was modified to 4:5:4:5. Retention of the stationary phase was 65%.

The possible cause of the sharp peaks may involve either the chemical nature of a particular solute or the effect of an exogenous agent in the solvent. The data obtained in Example 3 supported the latter. When the $BrAcT_3$ reaction mixture was eluted with the solvent system at a modified volume ratio of 4:5:4:5 (FIG. 3), retention times of both $BrAcT_3$ and the preceding $AcT_3$ peaks were increased as expected due to an increase in the relative polarity of the stationary phase. However, the $BrAcT_3$ peak became much broader, skewing toward the solvent front, recalling the appearance of the $BrAcT_4$ peak in FIG. 2. The preceding $AcT_3$ peak, on the other hand, had become much sharper. This indicates that the sharp peak profile of $BrAcT_3$ in FIG. 1 is not an inherent property of the compound but instead depends on the retention time of the solute. One way in which this could occur is if an agent present in the sample solution, but invisible to the detector, affects the partitioning of the $BrAcT_3$ peak. That this is indeed the case is strongly supported by our finding that reduction of the size of the initial sample of bromoacetylation product or its dilution yielded a normally broad $BrAcT_3$ peak. Finally, rechromatography of a sample of the collected peak also produced the same result.

Example 4

In order to prove this point further, a sample was run using the same derivation procedure but omitting $T_3$. Addition of this blank solution to a small amount of crude $BrAcT_3$ substantially increased the sharpness of the $BrAcT_3$ peak compared to that obtained when the $BrAcT_3$ alone was analyzed (not shown).

Figure 4:
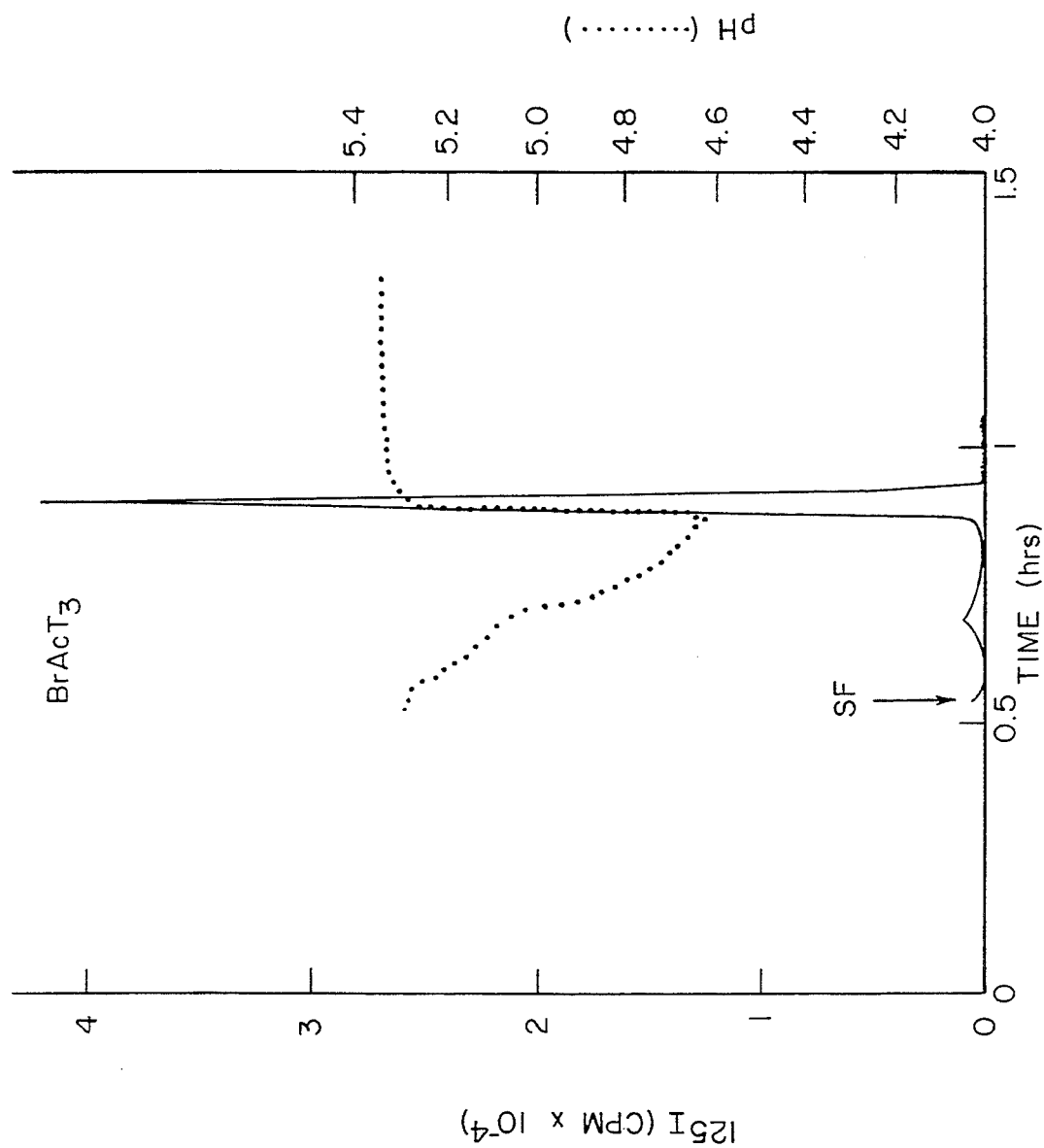
FIG. 4 is a chromatogram of BrAcT$_3$ obtained after addition of a blank bromoacetylation product (reaction mixture made without T$_3$).

FIG. 4 is a chromatogram of $BrAcT_3$ obtained after addition of the blank bromoacetylation product (reaction mixture made without $T_3$), using the standard 1:1:1:1 solvent system (pH 4). Note that the sharp $BrAcT_3$ peak coincides with the abrupt return point of the effluent pH shown by the dotted line. The sample solution was prepared by addition of 400 μl of blank bromoacetylation concentrate to $BrAcT_3$ concentrate corresponding to 0.025 mmol of $T_3$ and dissolution of this mixture in 4 ml of solvent. Other experimental conditions are the same as those described in Example 1. Retention of the stationary phase was 57%.

These results clearly indicate that an acidic component(s) present in the bromoacetylation solution creates a pH gradient in the CCC effluent, strongly affecting the sharpness of eluted $BrAcT_3$ peak. Mass spectrometric analysis of the blank bromoacetylation solution showed the presence of much methyl bromoacetate (as expected from the methanol workup) as well as appreciable amounts of bromoacetic acid.

Each of these components as well as other acids (HCl, TFA) were then tested to determine their ability to reproduce the characteristic pH change in the CCC effluent as well as the sharpness of the $BrAcT_3$ peak. Inorganic acids, including HCl and HBr, eluting rapidly due to their high polarity, did cause a sharp pH drop at the solvent front. Methyl bromoacetate failed to create any significant pH change in the CCC eluent. As expected, neither of these two groups of compounds produced a sharpened $BrAcT_3$ peak when added to a very dilute sample of the bromoacetylation product, i.e., one that produced a normal, broad $BrAcT_3$ peak. On the other hand, organic acids such as bromoacetic acid and TFA did cause a characteristic pH change in the effluent which was quite similar to that observed with the blank bromoacetylation solution. Furthermore, bromoacetic acid added to pure $BrAcT_3$ did indeed affect its elution profile.

Example 5

Figure 5:
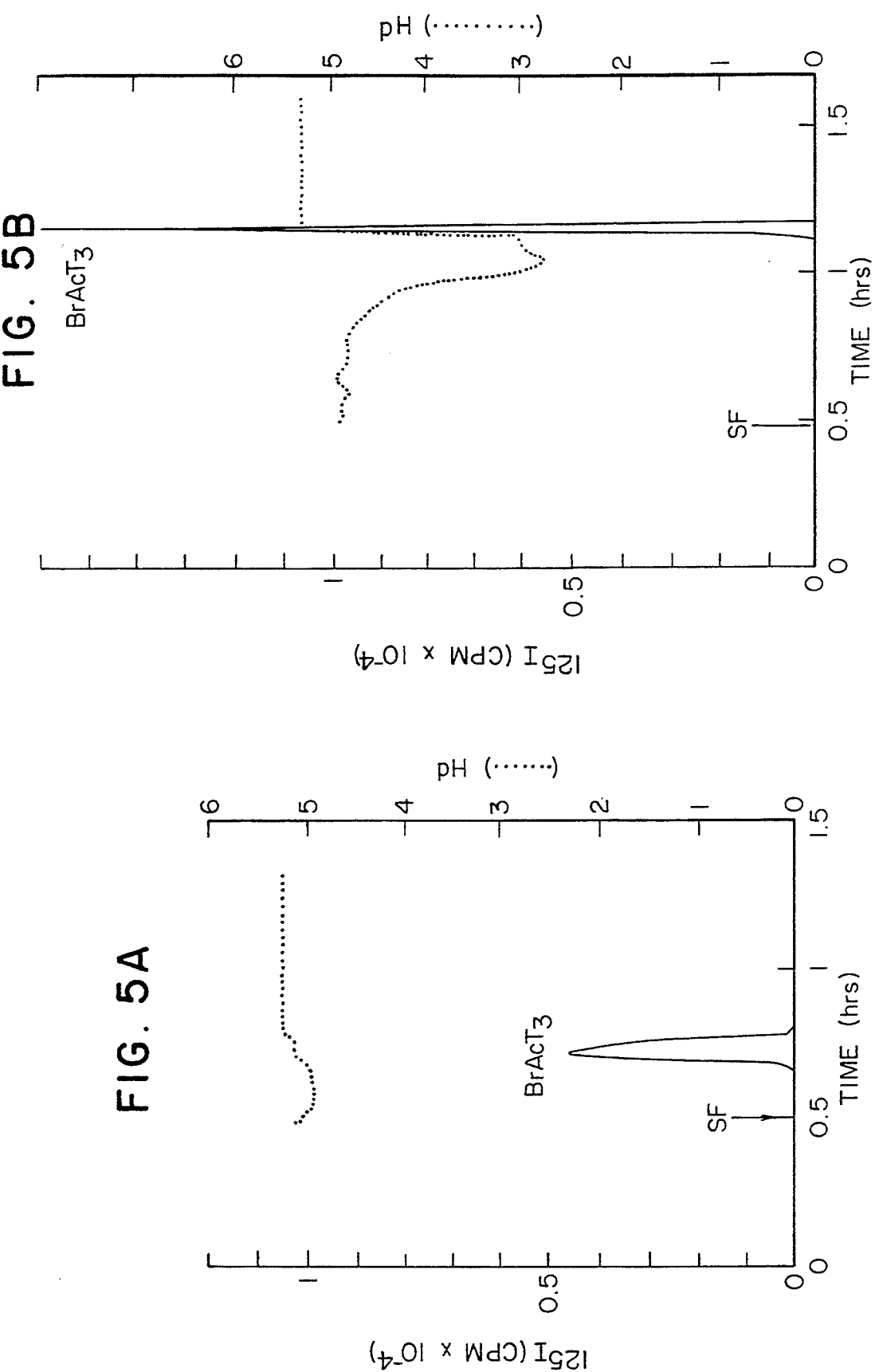
FIGS. 5A and 5B are chromatograms of pre-purified BrAcT$_3$ obtained without acid additives (A) and with 2.5 mmol of bromoacetic acid in the sample solution (B).

FIG. 5 is a chromatograph of pre-purified $BrAcT_3$ obtained without acid additives (A) and with 2.5 mmol bromoacetic acid (B) in the sample solution. The sharp peak profile of $BrAcT_3$ in FIG. 4 was reproduced by adding bromoacetic acid in the sample solution (B). Close association between the abrupt return point of the pH curve and the sharp $BrAcT_3$ peak shows that bromoacetic acid is the causative agent of the sharp peak. The sample solutions used were CCC-purified $BrAcT_3$ (ca 0.04 mmol) in 3.5 ml of the lower aqueous phase (A); and CCC-pre-purified $BrAcT_3$ (ca 0.04 mmol) and bromoacetic acid (2.5 mmol) in 3.5 ml lower phase (B). Other experimental conditions are described in Example 1. Retention of the stationary phase was 67% in A and 68% in B. In control experiment (A), where the sample solution contained no acid additives, $BrAcT_3$ was eluted in a relatively broad peak with a short retention time of about 40 min. Addition of 2.5 mmol of bromoacetic acid to the sample solution (B) produced a sharpened $BrAcT_3$ peak with a delayed elution time of 70 min. The pH curve displays a pattern similar to that produced by the blank bromoacetylation product (FIG. 4).

Figure 6:
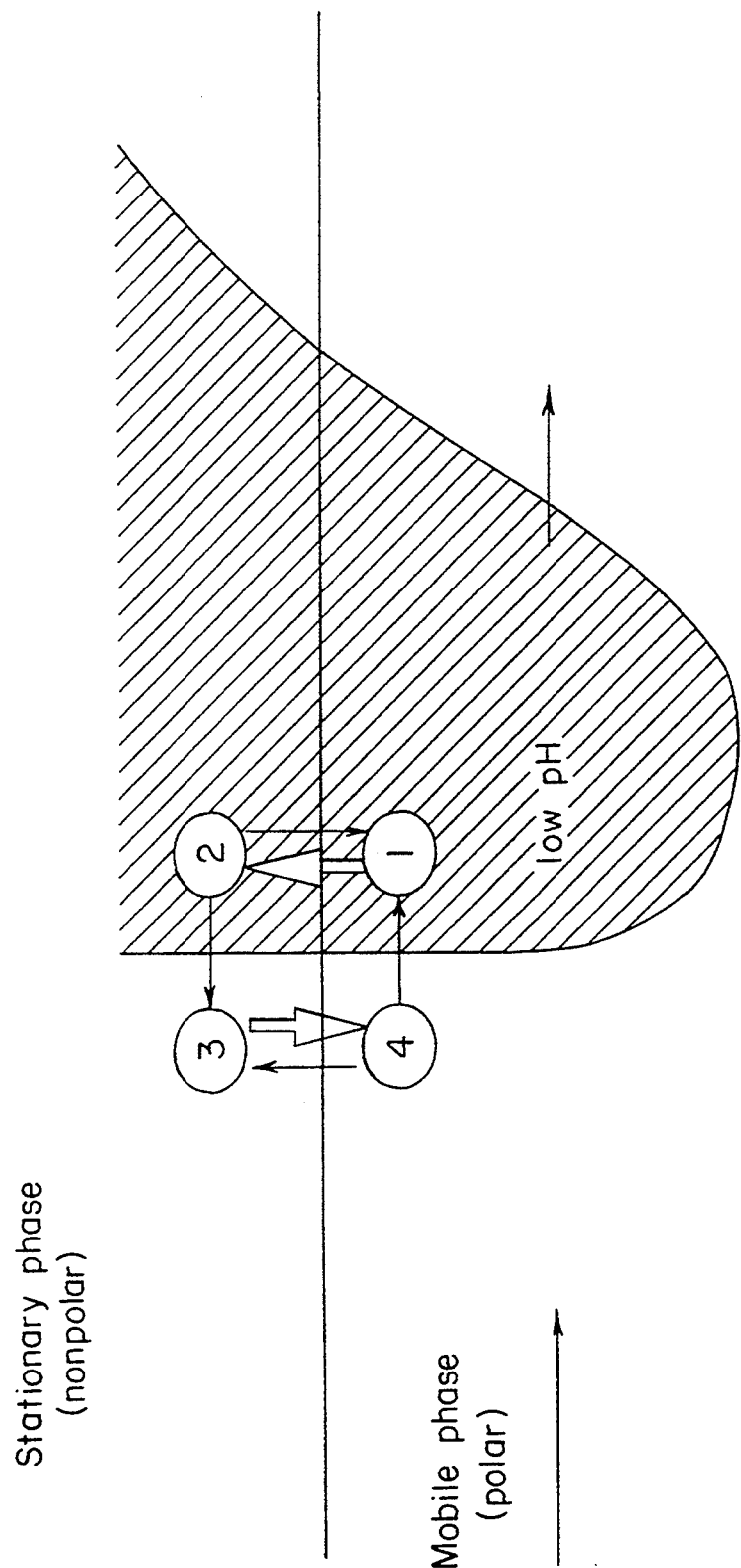
FIG. 6 is a schematic illustration of the peak sharpening process in the countercurrent chromatographic centrifuge.

As an explanation of this effect, FIG. 6 schematically illustrates a portion of the magnified chromatographic column which contains the retained nonaqueous stationary phase (upper half) and the flowing aqueous mobile phase (lower half). The shaded area represents a region of lowered pH caused by the acid introduced in the sample solution. Four numbers connected by arrows indicate the location and movement of the target solute around the sharp edge of the pH curve. When the solute is present at location 1, the low pH reduces the ionization and consequent polarity of the molecule forcing it to partition to the upper stationary phase. The solute thus moved to location 2 delays its movement relative to that of the low pH region. As the mobile phase moves forward, the solute finds itself in the relative location 3 where it is again exposed to a higher pH, increases its ionization and polarity, and returns to the aqueous mobile phase (location 4). In the mobile phase (location 4), the molecule quickly migrates into location 1 (low pH mobile phase) to repeat the above cycle. Consequently, the solute molecules are trapped in a narrow region across the diameter of the column at the sharp edge of the pH curve and eluted as a sharp peak immediately after the acid peak.

As shown in FIG. 2, $BrAcT_4$, an analog of $BrAcT_3$, elutes as a broad peak in spite of the fact that the sample solution also contains bromoacetic acid. This can be explained on the basis of the different partition coefficients of these two compounds (see FIG. 8). $T_3$ elutes before $T_4$ on $C_{18}$ reversed-phase HPLC. Similarly, BrAcT$_3$ is more hydrophobic than BrAcT$_3$ and therefore retained longer in the nonaqueous stationary phase, so that it is eluted from the column considerably later than bromoacetic acid. However, the elution time of the pH gradient can be adjusted by injecting the pH-gradient-forming agent into the column through the sample port at a selected time during the CCC run so that it elutes just before BrAcT$_3$. This possibility was examined by using TFA as a pH gradient-forming agent since it has a low boiling point (72.4° C.) and therefore is easily eliminated from the collected fractions by evaporation under reduced pressure.

Example 6

Figure 7A:
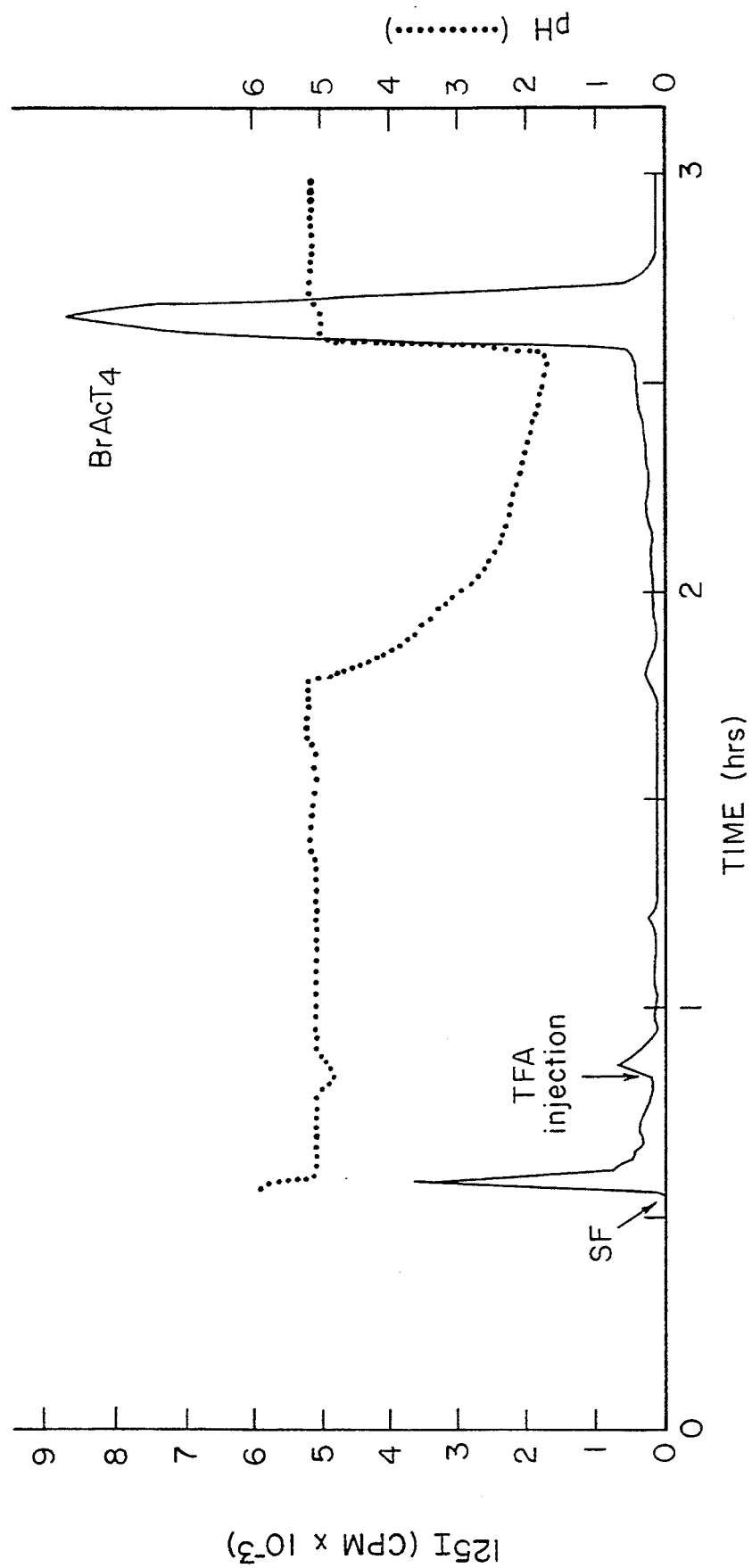
FIG. 7A is a chromatogram of BrAcT$_4$ obtained by injecting TFA at the middle of the CCC run.

FIG. 7A is a chromatogram of BrAcT$_3$ obtained by injecting TFA at the middle of the CCC run. A sharp BrAcT$_4$ peak was produced by a injection of 400 μl of TFA into the column after 150 ml of the mobile phase was eluted, much sharper than the peak observed in FIG. 2.

Figure 7B:
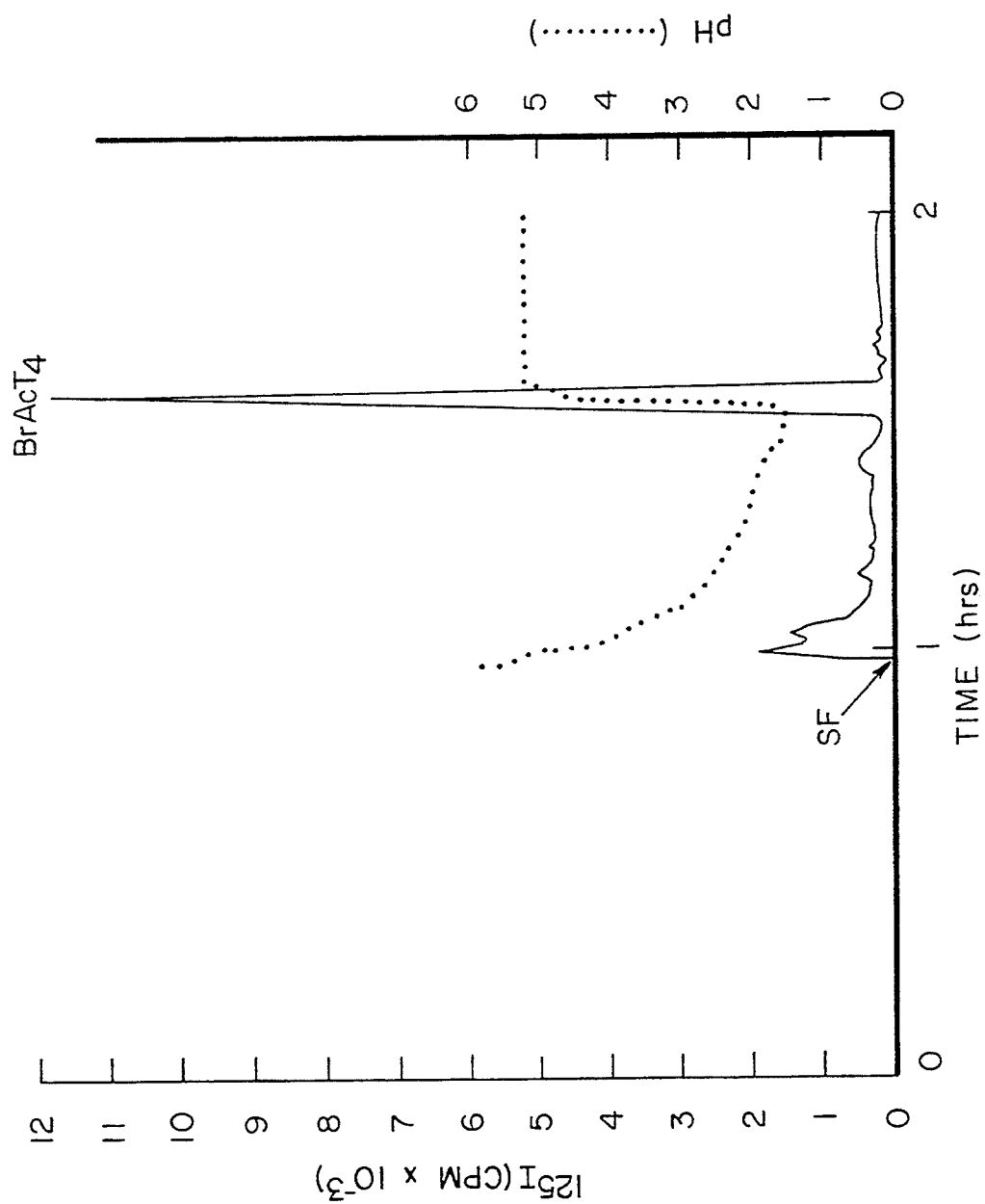
FIG. 7B is a chromatogram obtained by modifying the solvent ratio at 1:1:1:1 and introducing 400 μl of TFA in the sample solution.

An alternative and more effective technique for bringing about the same effect is to choose a suitable combination of the solvent system and gradient-forming organic acid in the sample solution so that the target solute is trapped into the low pH region during the fractionation as illustrated in FIG. 6. This scheme was effected by modifying the solvent ratio 1:1:1:1 and introducing TFA in the sample solution. FIG. 7B shows a chromatogram of CCC-pre-purified BrAcT$_4$ (about 0.04 mmol) obtained by adding 400 μl of TFA in the sample solution. Further studies have shown that the amount of TFA can be reduced to 200 μl for microgram quantities of BrAcT$_4$. It should be noted that in both chromatograms, elution of the BrAcT$_4$ peak coincides with the abrupt return point of the effluent pH shown by the dotted line. The sample solution was prepared by dissolving 0.04 mmol of CCC-pre-purified BrAcT$_4$ in 4 ml of the solvent and 400 μl of TFA (for chromatogram B). Experimental conditions including the solvent system, flow rate, revolution speed, etc. were identical to those described in FIG. 2. Retention of the stationary phase was 40% of the total column capacity in both separations.

The influence of the pH gradient described above can be observed with other organic acids as solutes. When the pH of the two-phase solvent system is substantially higher than the pK of the target solute, the majority of these acids exist in an ionized form favoring the polar aqueous phase during partition. When the solvent pH is reduced below the pK of the compound, the unionized acids partition more to the stationary nonaqueous phase. If performed near the pK of the target solute, chromatography with CCC tends to produce a broad peak, because more than one species is involved. In that case, a slight shift in the solvent pH in either direction would improve the sharpness of the solute involved.

Example 7

Figure 8:
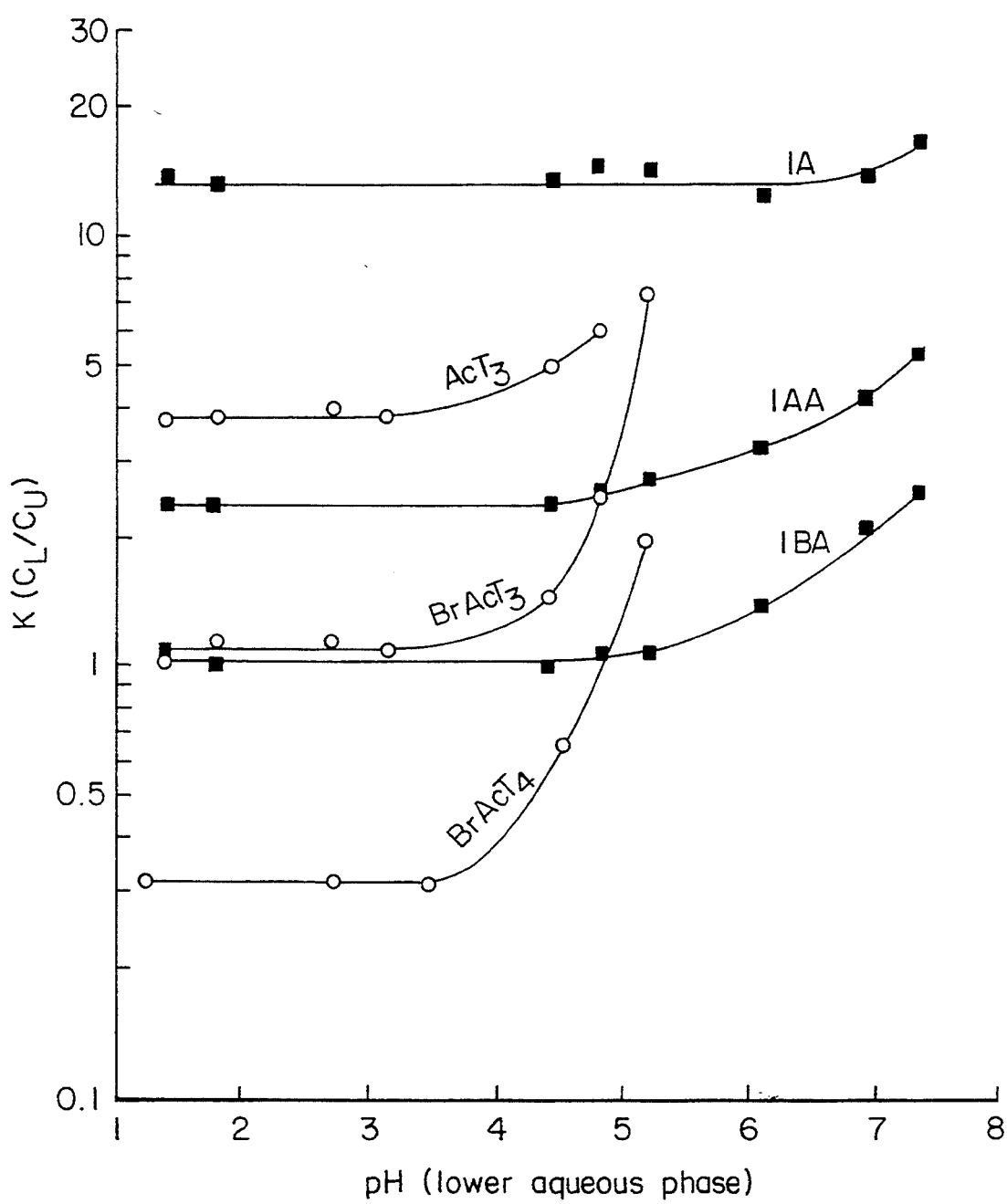
FIG. 8 is a graphic representation of the effects of pH on the K values of T$_3$ and T$_4$ derivatives, and of indole auxins in the solvent system hexane/ethyl acetate/methanol/15 mM ammonium acetate (1:1:1:1) while the solvent pH was adjusted by addition of HCl.

A set of indole auxins, IA, IAA, and IBA, were selected for further experiments since these compounds have suitable partition coefficients in the above two-phase solvent system. FIG. 8 shows the effect of pH on their partition coefficients compared to the effect on the K values of T$_3$ and T$_4$ derivatives. The standard solvent system, hexane/ethyl acetate/methanol/15 mM ammonium acetate (1:1:1:1), was used, where the solvent pH was adjusted by addition of HCl.

The K values of each compound are plotted against the pH in the lower aqueous phase. The two groups of compounds show different responses to the change of pH: All components show stable partition coefficients up to pH 3.5, however, the K values of all thyronine derivatives show a sharp increase between pH 4 and 5, whereas those of indole auxins display a gradual increase after pH 5–6, and are not significantly altered below pH 5–7. The results show that retention times and peak widths of the compounds in each group should be affected by a pH shift in those specific ranges.

Example 8

Figure 9B:
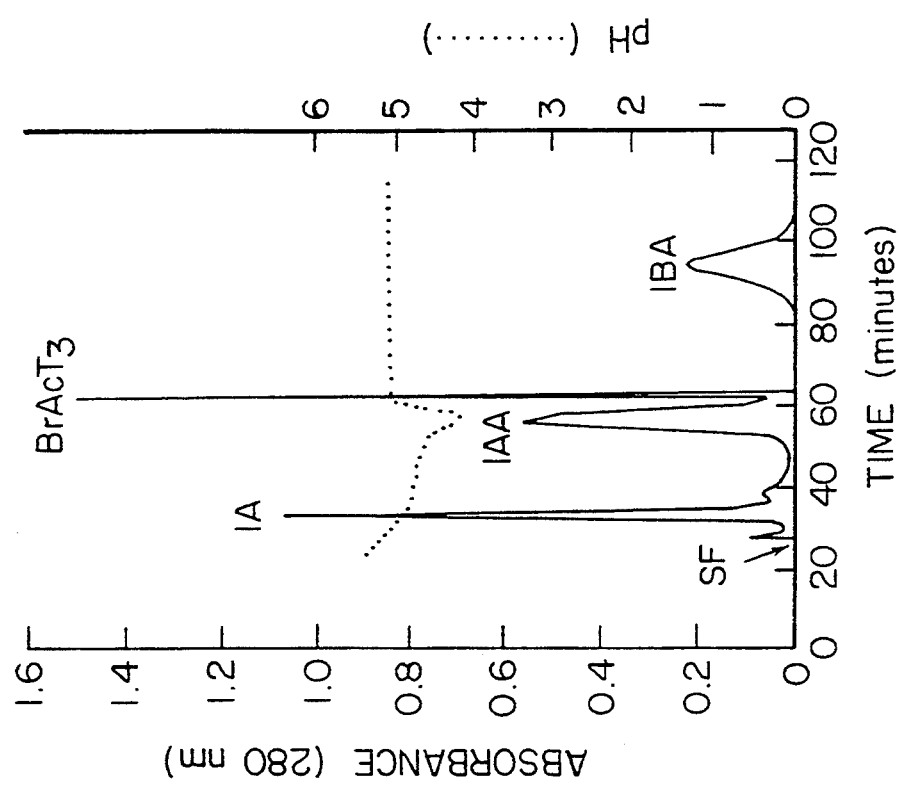
FIG. 9B is a chromatogram obtained under identical experimental conditions except that bromoacetic acid (1 mmol) was added to the sample solution.
Figure 9A:
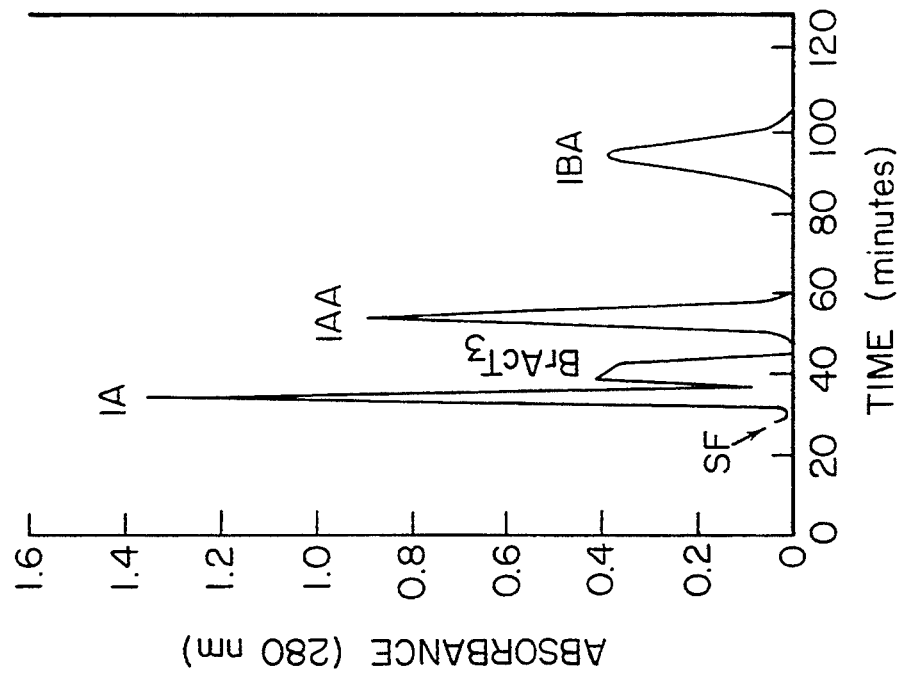
FIG. 9A is a chromatogram of a mixture of CCC-pre-purified BrAcT$_3$ (0.04 mmol) and indole auxins obtained with the standard solvent system.

FIG. 9 shows a pair of chromatograms emphasizing this point. A mixture of BrAcT$_3$ (CCC pre-purified) and indole auxins was chromatographed. The chromatogram in FIG. 9A was obtained from the sample mixture without acid additives, using the standard solvent system of hexane/ethyl acetate/methanol/15 mM ammonium acetate, pH 4 (1:1:1:1).

The three indole auxin peaks were well resolved and the broad BrAcT$_3$ peak eluted between the IA and IAA peaks. In order to observe the pH effect on the peak profile, bromoacetic acid (1 mmol) was added to the sample and the column was eluted with the same mobile phase used for FIG. 9A. The resulting chromatogram shown in FIG. 9B revealed a remarkable change in the BrAcT$_3$ peak which became much sharper and was only eluted after IAA, i.e., its elution was delayed. In contrast, the three indole auxin peaks were little affected by the pH shift.

Example 9

Figure 10A:
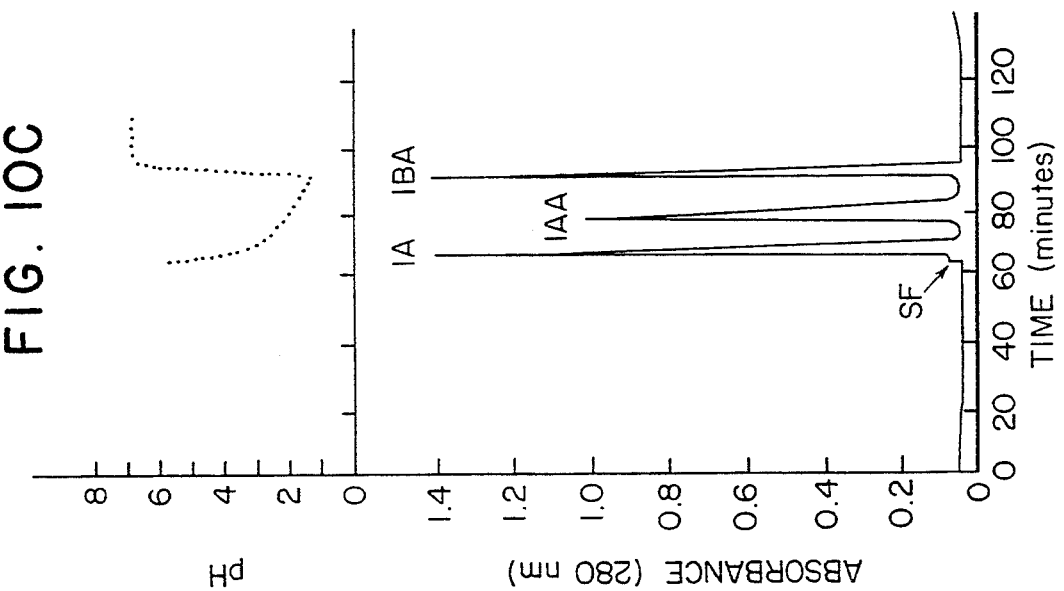
FIGS. 10A, 10B, and 10C are chromatograms of indole auxins obtained with a neutral solvent system using sample mixtures containing TFA in amounts of 2 μl (A), 100 μl (B) and 400 μl (C).
Figure 10B:
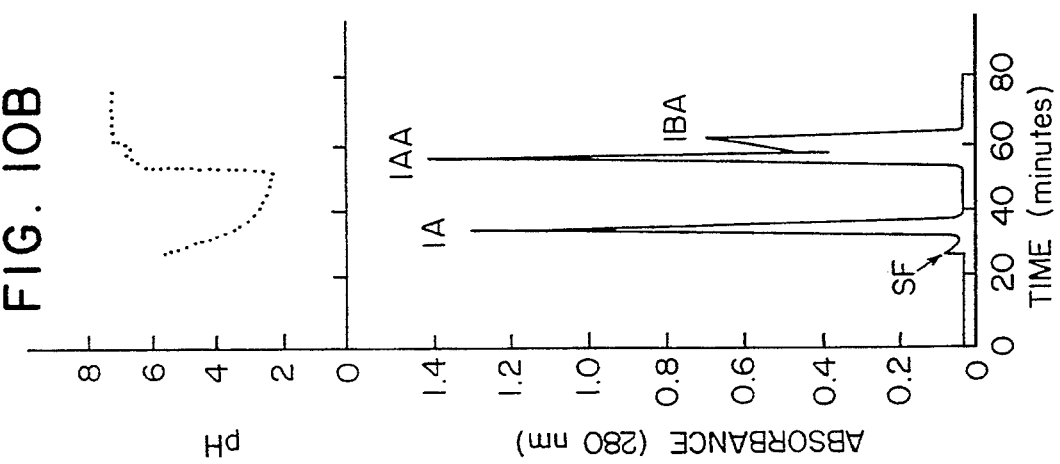
Figure 10C:
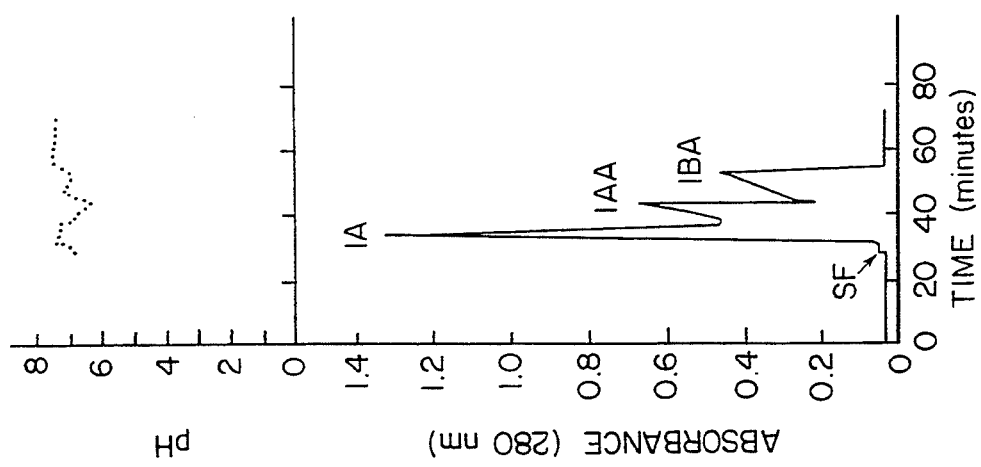

In order to examine the effect of a pH change on the peak profile of the indole auxins, their fractionation by CCC was performed with the same solvent system adjusted to pH 7. Without added acids, the sample produced broad skewed peaks and a relatively short elution time for IAA and IBA. Addition of a trace amount (2 μl) of TFA (FIG. 10A) failed to improve the peak sharpness, however, 100 μl of TFA added to the sample solution (FIG. 10B) sharpened the IAA peak which eluted immediately after the abrupt pH return point. The IBA peak eluting later showed little change, maintaining a broad peak profile. A further increase of TFA (400 μl) (FIG. 10C) resulted in a considerable shift of the pH curve toward longer times to coincide with the elution of the third peak (IBA). Consequently, the IBA peak was greatly sharpened while the second IAA peak returned to the normal profile as seen in FIG. 9A.

As observed in FIG. 10 (upper diagrams), the profile of the pH curve is greatly influenced by the amount of TFA introduced in the sample solution: An increased amount of TFA results in a lower pH and longer persistence of the low pH. The higher TFA concentration produces relatively more unionized, less polar species which go into the stationary organic phase. Hence, increased TFA concentration results in a longer retention time and more intense skewing of the pH elution curve. Retention of the stationary phase was 67% (A), 68% (B) and 28% (C). The low stationary phase retention in C is presumably due to the introduction of a large volume of TFA in the sample solution.

This sample method of adding TFA or other acid may be useful not only in CCC fractionation but also in other chromatographic methods, since addition of an appropriate reagent to the sample can produce peak sharpening and delayed elution of the target compound(s). The method may work as well for basic compounds by using a weak base to establish the pH profile. However, the peak sharpening obtained is not necessarily accompanied by increased resolution of components, as shown by the mixture of compounds found in the sharp peak of FIG. 2. Nonetheless, increasing the concentration of the sample allows easier detection and the advantageous collection of samples in a minimum volume of eluting solvent. Changing the elution time can often be helpful in avoiding co-elution of impurities. This will occur as long as the impurities do not respond to the pH change in a similar fashion. While the technique is obviously effective in shifting organic acids and bases away from neutral compounds, it may also be used in separating these classes of compounds from salts. If a co-eluting salt is completely ionized at all pH values ($NaCl$, $Na_2SO_4$, $NaSO_3R$), an adjustment of pH in either direction will easily separate it from the desired solute. On the other hand, if the salt is subject to hydrolysis, adjustment of pH is more critical.

Example 10

Figure 11:
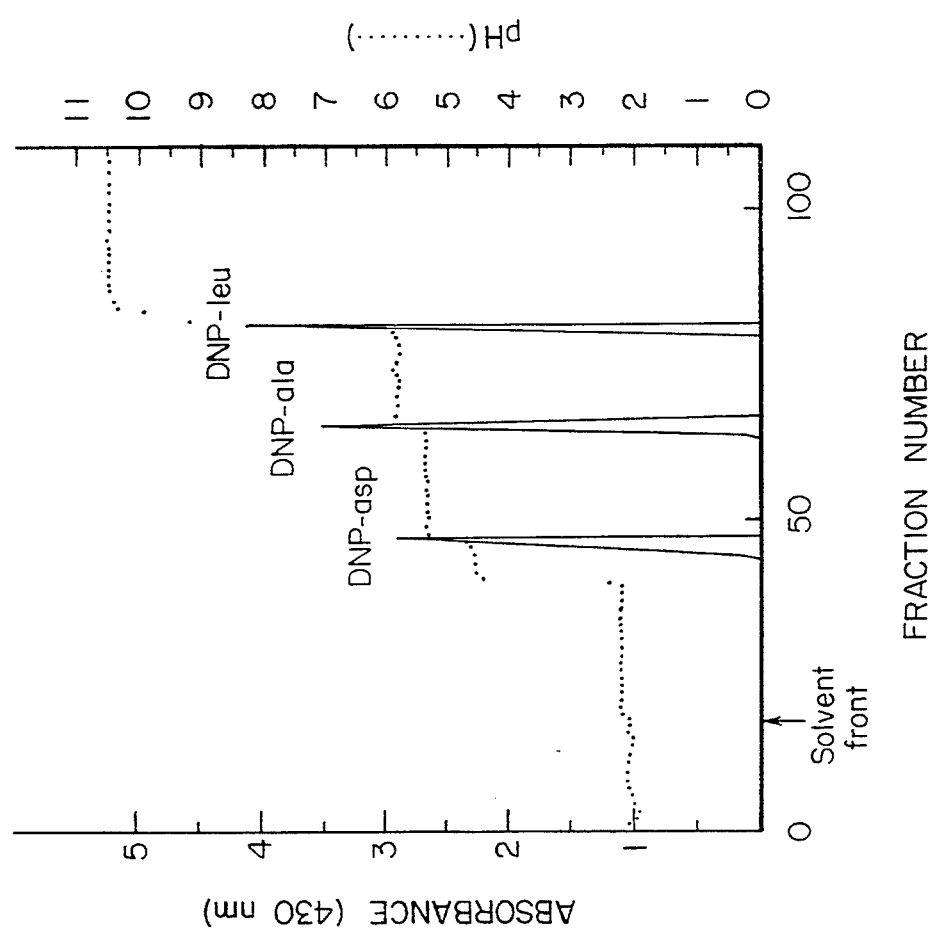
FIG. 11 is a chromatogram of a mixture of DNP-L-aspartic acid, DNP-L-alanine, and DNP-L-leucine obtained with a MTBE/acetonitrile/water solvent system, by adding four organic acids, acetic acid, propionic acid, n-butyric acid, and trifluoroacetic acid, to the stationary phase.

Sharp elution peaks are also produced by adding one or more organic acids in the stationary upper phase. FIG. 11 shows a chromatogram of DNP-amino acids obtained from a two-base solvent system composed of methyl tertiary butyl ether, acetonitrile, and water (4:1:5 by volume). The separation was performed as follows: The solvent mixture was equilibrated in a separatory funnel at room temperature. After the two phases were separated, the upper phase was acidified by adding four organic acids, i.e., acetic acid, propionic acid, n-butyric acid and trifluoroacetic acid, each 200 $\mu$l per 500 ml of the upper phase. The pH of the lower aqueous mobile phase was raised to 10.77 by adding ammonium hydroxide at a concentration of 0.1%. The column was first completely filled with the above stationary upper phase and the sample solution containing 1 mg each of DNP-L-aspartic acid (DNP-asp), DNP-L-alanine (DNP-ala) and DNP-L-leucine (DNP-leu), was introduced through the sample port. Then, the column was eluted with the mobile aqueous phase at a flow rate of 3 ml/min while the column was rotated at 800 rpm. The organic acids introduced into the stationary phase formed 4 acidic pH plateaus as indicated by a dotted line. The three DNP-amino acids were completely separated, each forming a sharp elution peak at the transitional zone between the pH plateaus.

Sharp peaks of basic compounds may be similarly produced by adding an organic base in the stationary phase.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for concentrating a solute from a mixture by countercurrent chromatography, comprising:
   (a) introducing a stationary phase into a countercurrent chromatographic centrifuge;
   (b) introducing a sample of a mixture containing a solute into said countercurrent chromatographic centrifuge;
   (c) introducing a sufficient quantity of an elution peak sharpening agent that causes a pH profile to form across the stationary phase-mobile phase boundary that traps solute molecules in a sharp edge of a pH curve, so that the solute molecules elute as a sharp peak into said countercurrent chromatographic centrifuge;
   (d) introducing a mobile phase into said countercurrent chromatographic centrifuge;
   (e) performing countercurrent chromatographic centrifugation of said mobile phase and eluting fractions of said mobile phase from said countercurrent chromatographic centrifuge; and
   (f) identifying and collecting the eluting fractions containing the concentrated solute.

2. The method according to claim 1, wherein said elution peak sharpening agent is introduced with said sample of said mixture containing said solute.

3. The method according to claim 1, wherein said elution peak sharpening agent is introduced in said stationary phase.

4. The method according to claim 1, wherein said solute is an organic acid or base.

5. The method according to claim 4, wherein said organic acid solute is selected from the group consisting of N-bromoacetyl-3,3',5-triiodo-L-thyronine, indole auxins, DNP-L-aspartic acid, DNP-L-alamine, and DNP-L-leucine.

6. The method according to claim 1, wherein said elution peak sharpening agent is a base.

7. The method according to claim 1, wherein said elution peak sharpening agent is an acid.

8. The method according to claim 7, wherein said elution peak sharpening agent is a carboxylic acid.

9. The method according to claim 8, wherein said elution peak sharpening agent is selected form the group consisting of bromoacetic acid, trifluoroacetic acid, acetic acid, propionic acid, butanoic acid, and mixtures thereof.

10. The method according to claim 1, wherein said stationary phase comprises a non-polar organic solvent.

11. The method according to claim 1, wherein said mobile phase comprises a polar solvent.

12. The method according to claim 1, wherein said sample of said mixture containing said solute is prepared by dissolving said mixture into an aliquot of a non-polar organic solvent or mixture thereof with other non-polar or polar solvents.

13. The method according to claim 1, wherein said stationary phase and said mobile phase are prepared by mixing hexane, ethyl acetate, methanol, and an aqueous solution of 15 mM ammonium acetate, thoroughly equilibrating said mixture at room temperature, separating the resulting organic and aqueous phases, introducing said organic phase into said countercurrent chromatographic centrifuge as said stationary phase, and introducing said aqueous phase into said countercurrent chromatographic centrifuge as said mobile phase.

14. A method for concentrating on organic solute from a mixture by countercurrent chromatography, comprising:
   (a) introducing a stationary phase, comprising a non-polar organic solvent into a countercurrent chromatographic centrifuge;
   (b) introducing a sample of a mixture containing an organic solute into said countercurrent chromatographic centrifuge;
   (c) introducing a sufficient quantity of an acidic or basic elution peak sharpening agent that causes a pH profile to form across the stationary phase-mobile phase boundary that traps solute molecules in a sharp edge of a pH curve, so that the solute molecules elute as a sharp peak into said countercurrent chromatographic centrifuge;

(d) introducing a mobile phase into said countercurrent chromatographic centrifuge;

(e) performing countercurrent chromatographic centrifugation of said mobile phase and eluting fractions of said mobile phase from said countercurrent chromatographic centrifuge;

(f) monitoring the pH of said eluting fractions; and (g) identifying and collecting those eluting fractions containing said concentrated solute.

15. The method according to claim 14, wherein said organic solute is an organic acid, and said acidic elution peak sharpening agent is introduced with said sample of said mixture containing said solute, and wherein said identifying and collecting of said eluting fractions containing said concentrated solute comprises collecting fractions which elute between the time that the pH of said fractions has reached a minimum, and the time when the pH of said fractions has become approximately constant.

16. The method according to claim 15, wherein said organic acid solute is selected from the group consisting of N-bromoacetyl-3,3',5-triiodo-L-thyronine, indole auxins, DNP-L-aspartic acid, DNP-L-alanine, and DNP-L-leucine.

17. The method according to claim 15, wherein said acidic elution peak sharpening agent is selected from the group consisting of bromoacetic acid, trifluoroacetic acid, acetic acid, propanoic acid, butanoic acid, and mixtures thereof.

18. The method according to claim 14, wherein said organic solute is an organic base, and wherein said basic elution peak sharpening agent is introduced with said sample of said mixture containing said solute, and wherein said identifying and collecting of said eluting fractions containing said concentrated solute comprises collecting fractions which elute between the time that the pH of said fractions reaches a maximum, and the time when the pH of said fractions has become approximately constant.

19. The method according to claim 14, wherein an acidic or basic peak elution agent is introduced into said stationary phase, and said identifying and collecting of said eluting fractions comprises collecting fractions which elute during transitional zone between two different, approximately constant pH levels.

* * * * *